(12) United States Patent
Strecker

(10) Patent No.: US 6,585,756 B1
(45) Date of Patent: Jul. 1, 2003

(54) IMPLANTABLE LUMEN PROSTHESIS

(76) Inventor: Ernst P. Strecker, Vierordt Str 7A 76228, Karlsruhe (DE)

( * ) Notice: Subject to any disclaimer, the term of this patent is extended or adjusted under 35 U.S.C. 154(b) by 0 days.

(21) Appl. No.: 09/311,965

(22) Filed: May 14, 1999

(51) Int. Cl.[7] .................................................. A61F 2/06
(52) U.S. Cl. ...................... 623/1.16; 623/1.35; 623/1.36
(58) Field of Search ............................... 623/1.13, 1.15, 623/1.16, 1.27, 1.35, 1.36; 606/200

(56) References Cited

U.S. PATENT DOCUMENTS

| | | | |
|---|---|---|---|
| 4,425,908 A | 1/1984 | Simon | 128/1 |
| 4,793,348 A | 12/1988 | Palmaz | 128/325 |
| 4,994,071 A | 2/1991 | MacGregor | 606/194 |
| 5,211,658 A | 5/1993 | Clouse | 623/1 |
| 5,354,308 A | 10/1994 | Simon et al. | 606/198 |
| 5,360,401 A | 11/1994 | Turnland | 604/96 |
| 5,360,443 A | 11/1994 | Barone et al. | 623/1 |
| 5,375,612 A | 12/1994 | Cottenceau et al. | 128/899 |
| 5,382,261 A | 1/1995 | Palmaz | 606/158 |
| 5,387,235 A | 2/1995 | Chuter | 623/1 |
| 5,395,390 A | 3/1995 | Simon et al. | 606/198 |
| 5,540,712 A | 7/1996 | Kleshinski et al. | 606/198 |
| 5,562,724 A | 10/1996 | Vorwerk et al. | 623/1 |
| 5,562,726 A | 10/1996 | Chuter | 623/1 |
| 5,571,135 A | 11/1996 | Fraser et al. | 606/198 |
| 5,609,627 A | 3/1997 | Goicoechea et al. | 623/1 |
| 5,626,599 A | 5/1997 | Bourne et al. | 606/194 |
| 5,626,605 A | 5/1997 | Irie et al. | 606/200 |
| D380,831 S | 7/1997 | Kavteladze et al. | D24/155 |
| 5,656,036 A | 8/1997 | Palmaz | 623/12 |
| 5,669,933 A | 9/1997 | Simon et al. | 600/200 |
| 5,669,936 A | 9/1997 | Lazarus | 623/1 |
| 5,676,696 A | 10/1997 | Marcade | 623/1 |
| 5,676,697 A | 10/1997 | McDonald | 623/1 |
| 5,683,450 A | 11/1997 | Goicoechea et al. | 623/1 |
| 5,695,519 A | 12/1997 | Summers et al. | 606/200 |
| 5,713,917 A | 2/1998 | Leonhardt et al. | 606/194 |
| 5,716,365 A | 2/1998 | Goicoechea et al. | 606/108 |
| 5,746,765 A | 5/1998 | Kleshinski et al. | 606/198 |
| 5,746,767 A | 5/1998 | Smith | 606/200 |
| 5,795,322 A | 8/1998 | Boudewijn | 604/22 |
| 5,800,457 A | 9/1998 | Gelbfish | 606/200 |

(List continued on next page.)

FOREIGN PATENT DOCUMENTS

| | | |
|---|---|---|
| DE | 195 31 659 A 1 | 3/1997 |
| EP | 0 647 148 B1 | 1/1994 |
| EP | 0 653 924 B1 | 2/1994 |
| EP | 0 880 948 A1 | 12/1998 |
| EP | 1 000 590 A1 | 5/2000 |
| WO | WO 97/09945 | 3/1997 |
| WO | WO 98/06355 | 2/1998 |
| WO | 98/07389 * | 2/1998 |
| WO | WO 98/33454 | 8/1998 |
| WO | WO 98/47447 | 10/1998 |
| WO | WO 99/00055 | 1/1999 |
| WO | WO 99/39662 | 8/1999 |
| WO | WO 99/47071 | 9/1999 |

OTHER PUBLICATIONS

Brochure, "A decision for precision," ZA–STENT, Cook, Listen Understand Innovate.

*Primary Examiner*—Bruce Snow
(74) *Attorney, Agent, or Firm*—Crompton, Seager & Tufte LLC

(57) ABSTRACT

The present invention relates to an implantable prosthesis having a membrane and a fluid channel that are inserted into a body lumen to maintain fluid flow and support the lumen wall. A preferred embodiment of the invention includes a mesh membrane or filter attached to a covered stent. The membrane can be mounted on a frame formed with a shape memory material that can be delivered through a catheter into a body lumen. The membrane and the frame can expand from a delivery state into an expanded state.

14 Claims, 15 Drawing Sheets

U.S. PATENT DOCUMENTS

| | | |
|---|---|---|
| 5,800,515 A | 9/1998 | Nadal et al. .................... 623/1 |
| 5,800,519 A | 9/1998 | Sandock ........................ 623/1 |
| 5,800,525 A | 9/1998 | Bachinski et al. ............. 623/1 |
| 5,824,055 A | 10/1998 | Spiridigliozzi et al. ........ 623/1 |
| 5,836,968 A | 11/1998 | Simon et al. ............... 606/200 |
| 5,843,160 A | 12/1998 | Rhodes .......................... 623/1 |
| 6,152,956 A * | 11/2000 | Pierce ....................... 623/1.13 |
| 6,306,164 B1 * | 10/2001 | Kujawski ................... 623/1.35 |
| 6,348,066 B1 * | 2/2002 | Pinchuk et al. ............ 623/1.16 |

* cited by examiner

IMPLANTABLE LUMEN PROSTHESIS

BACKGROUND OF THE INVENTION

Various prosthetic devices have been developed for the treatment of vascular disease. These include self expanding stents that can be compressed and introduced into the vascular system using catheters. When the catheter is positioned percutaneously or by other techniques at the required site, the stent is released and the catheter is withdrawn.

The stents or prostheses have been developed to treat particular forms of vascular disease including weakened or occluded blood vessels or arteries. The treatment of a stenosis or aneurysm, for example, using a tubular prosthesis can reduce the risk of an embolism or rupture of the aneurysm. In an abdominal aortic aneurysm, for example, a bifurcated tubular sleeve can be used to maintain blood flow between the aortic artery and the iliac arteries.

However, a continuing need exists for further improvements in devices and methods of using implantable prostheses for the treatment of various conditions.

SUMMARY OF THE INVENTION

This invention relates to an implantable prosthesis including a membrane or filter and a fluid flow channel to control the flow of fluid through a body lumen. A preferred embodiment of the invention uses a mesh membrane connected to a stent and, more particularly, to a stent used to bypass an aneurysm. In a preferred embodiment of the invention, the fluid flow channel, or stent, is coupled to the filter. The device includes, in a preferred embodiment, a frame having a plurality of struts, the struts conforming to the shape of the inner wall of a vessel, a membrane covering the struts, at least one tubular prosthesis or stent being aligned with and connected to an aperture in the membrane and an attaching mechanism that connects the membrane to the tubular section.

In one embodiment, the device is collapsible to fit inside a catheter. In a preferred embodiment, the device is collapsible to a diameter of 12 French or less. The frame and/or the tubular prosthesis can be a device such as that described in International Application No. PCT/DE/00226 filed on Jan. 24, 1998, and also described in U.S. application Ser. No. 09/250,714, filed on Feb. 16, 1999 the entire contents of these applications being incorporated herein by reference. The stent and the frame of the filter or membrane can comprise a shape memory material such as a nickel-titanium alloy.

In a preferred embodiment, the frame comprises a double coil as described and illustrated in the above incorporated applications. One of the coils can be covered with a membrane material. In one embodiment, there can be an oblique angle between the two coils up to and including, for example, a 90-degree angle.

The struts of the frame can radiate outwardly from a center point of the frame. In this embodiment, the perimeter formed by the struts conforms to the shape of the inner wall of a vessel. In a preferred embodiment, the shape of the perimeter formed by the struts is circular. In another preferred embodiment, the struts comprise a plurality of loop shapes.

The membrane material can comprise either a mesh material or a non-permeable material. In a preferred embodiment, the membrane material extends beyond the perimeter formed by the struts of the frame. The additional membrane material allows the vessel to become completely sealed to prevent leakage between the membrane and the vessel wall.

The stent can comprise a flexible material. In a preferred embodiment, the device comprises two stents to be used to bypass an aneurysm located at a bifurcation. The stent can also comprise an attachment mechanism to secure an end of the stent to the membrane.

The stent can be attached to the membrane and/or a vessel wall using an adhesive such as a polymer. The polymer can also be used to secure the stent to a double coil membrane. After insertion of the prosthesis, the adhesive can be injected in fluid form into the cavity with a catheter and then hardened in situ.

The invention also relates to a method for treating a body lumen using an implantable prosthesis. The invention can relate to a method for deploying a prosthesis within a body lumen. This method can include the use of one or more catheters to deploy the elements of the prosthesis. The invention can also relate to a method for attaching at least one stent to a membrane. This method can involve deploying a membrane in a vessel, forming an opening or aperture in the membrane, and connecting a stent to the membrane wherein the tubular path through the stent is coaxially aligned with the aperture.

Figure 1:
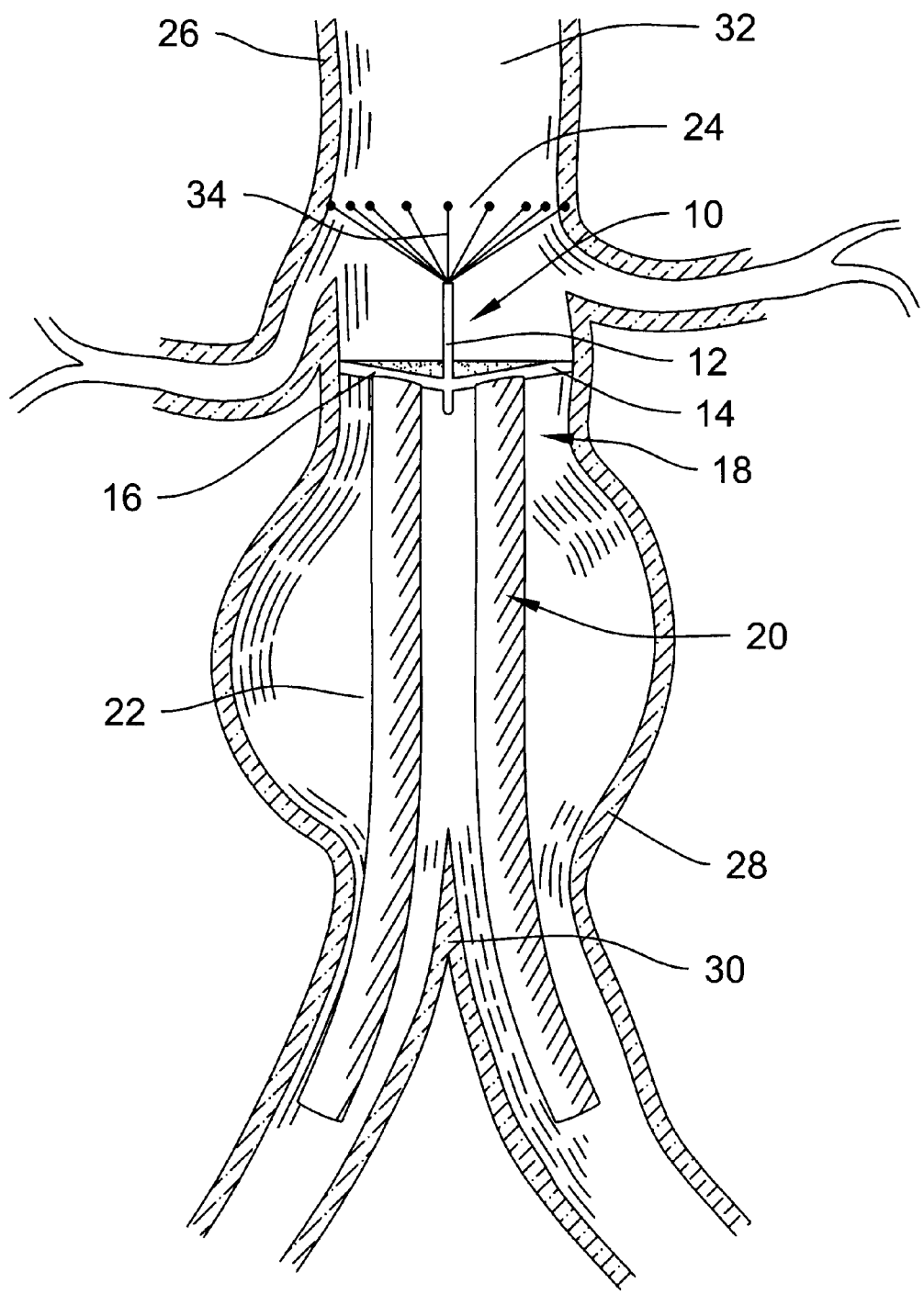
FIG. 1 illustrates a cross sectional lateral view of an aneurysm stent secured within an aorta.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

FIG. 1 illustrates an embodiment of an aneurysm stent 10. In this embodiment, the aneurysm stent 10 comprises a frame 12 having a plurality of struts 14 and being covered by a membrane 16. The frame 12 can comprise any biocompatible material. A bifurcation stent 18 comprising a first stent portion 20 and a second stent portion 22 form an aperture in the membrane 16 and are secured therein. Also in this embodiment, the aneurysm stent 10 comprises a securing mechanism 24 which secures the stent 10 to an aorta wall 26.

In one embodiment, the aneurysm stent 10 is collapsible to fit inside a catheter. In a preferred embodiment, the stent 10 is collapsible to a diameter of 12 French. The frame 12, membrane 16 and securing mechanism 24 can comprise a shape memory material. In this embodiment, the frame 12, when removed from a catheter, expands into a predetermined shape.

The struts 14 of the frame 12 can radiate outwardly from a center point of the frame 12. In this embodiment, the perimeter formed by the struts 14 form a shape which conforms to the shape of the inner wall of an aorta wall 26. In a preferred embodiment, the shape of the perimeter formed by the struts 14 is circular. In another preferred embodiment, the struts 14 comprise a plurality of loop shapes.

The membrane 16 can comprise either a mesh material or a non-permeable material. The mesh material can allow for obstruction of clots while allowing the flow of fluids through the vessel. The non-permeable material occludes the flow of any substance through the vessel.

The mesh material can have mesh holes the size of 0.2 to 1.0 mm. In one embodiment, the mesh is knitted or weaved. In this embodiment, when the stent 10 is inserted into a lumen, the lumen walls will cause the stent 10 to compress, thereby causing the mesh holes to become smaller.

To create a sealing between the frame 12 and the first 20 and second stent portions 22, the mesh material can be thrombogenic. The sealing can be created by a rough texture of the surface of the mesh material. In one embodiment, the rough texture is created by a textile material like wool. The rough texture can also be created by a material where the mesh filaments consist of multiple threads. The sealing can also be created by covering the mesh filaments with a thrombogenic substance or a sealing drug. In an alternate embodiment, the sealing can be created when the mesh filaments are made of an elastic material, such as silicone, or when the mesh filaments are formed of textile filaments and elastic filaments.

In a preferred embodiment, the membrane 16 material extends beyond the perimeter formed by the struts 14 of the frame 12. The additional membrane material 16 allows the vessel to become completely sealed.

The first stent portion 20 and the second stent portion 22 of the bifurcation stent 18 can comprise a flexible material.

In a preferred embodiment, the device comprises two stents to be used to bypass an aneurysm 28 located at a bifurcation 30. In this preferred embodiment, first stent portion 20 and the second stent portion 22 of the bifurcation stent 18 carries blood from the aorta 32, past the aneurysm 29 and to the bifurcation 30. This process reduces the pressure at the aneurysm site 29 and will help prolong the life of the aneurysm 29. The process will also help to decrease the risk of aneurysm 29 rupture. The first 20 and second 22 stent portions of the bifurcation stent 18 can be made from a mesh material. This material can be, but is not limited to, a fabric material or a plastic material.

The securing mechanism 24, in one embodiment, comprises a series of arms or connectors 34 which attach the aneurysm stent 10 to the aorta wall 26. This can be accomplished using small hooks or barbs.

Figure 2:
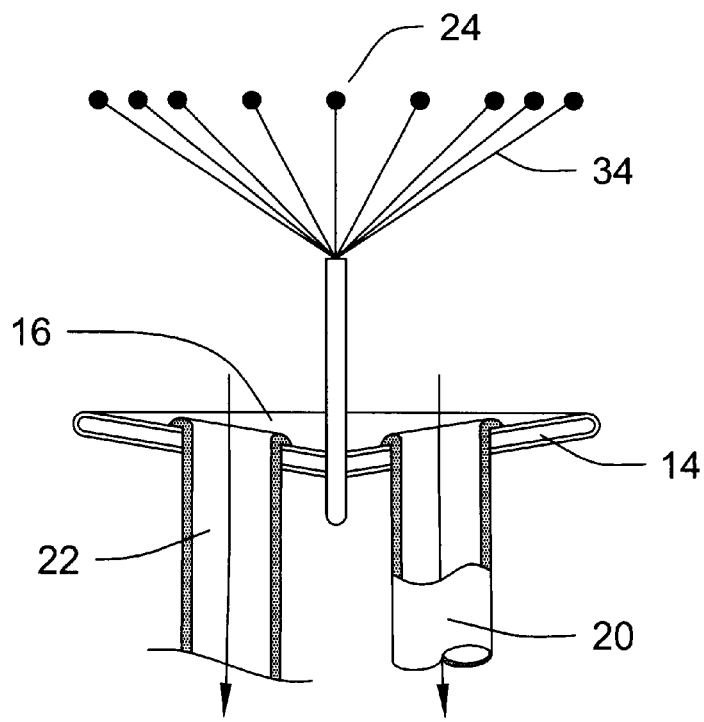
FIG. 2 illustrates an embodiment of the stent portions attachment to a membrane

FIG. 2 illustrates a preferred embodiment of the first 20 and second 22 stent portions attachment to the membrane 16. In this embodiment, the proximal ends of the stents 20, 22 are funnel shaped which prevents the stents 20, 22 from translating past the membrane 16. In an alternate embodiment, the ends of the stents 20, 22 comprise a plurality of anchors which also prevent migration of the stents 20, 22. In an alternate embodiment, the proximal ends of the stents 20, 22 are tapered. In a preferred embodiment, the ends can be reduced in area by 5%–15%, for example.

Figure 3:
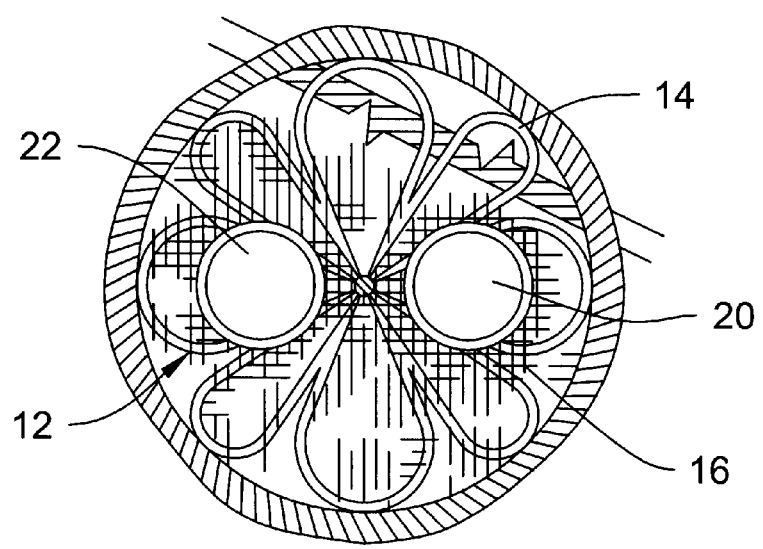
FIG. 3 shows a top view of an aneurysm stent secured within an aorta.

FIG. 3 illustrates a top view of the aneurysm stent 10. In this embodiment, the loop pattern of the struts 14 of the frame 12 is shown. Membrane material 16, in this embodiment, hangs past the perimeter created by the struts 14 to create a secure seal of the aneurysm stent 10 when placed in an aorta.

Figure 4:
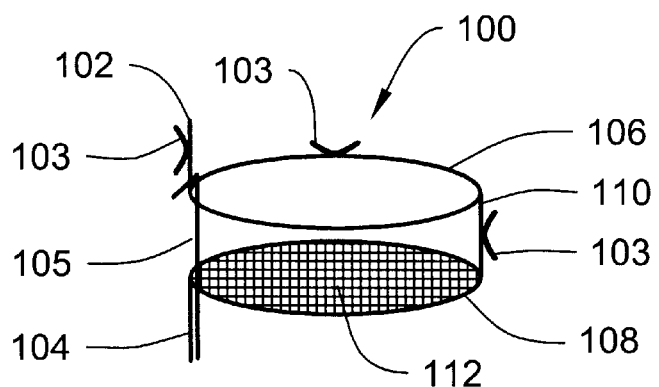
FIG. 4 shows an oblique view of a double coil stent in an expanded state.

FIG. 4 illustrates an oblique view of a double coil stent 100 in an expanded state. In an embodiment of the invention, the double coil stent 100 has a first end 102 and a second end 104. The stent 100 also include a first coil 106 and a second coil 108. In a preferred embodiment, the first 106 and second 108 coils can have an oblique or circular shaped. The first 106 coil and second 108 coils can be used to support the inner wall of a vessel, such as an artery.

The coils 106 and 108 of the double coil 100 are attached at a connection site 110. There can be a 90-degree angulation between the connection site 100 and the first 106 and second 108 coils in the stent's 100 expanded state. In a preferred embodiment, the connection site 110 consists of two wires, one wire derived from the first coil 106 and the second wire derived from the second coil 108. The two wires can be connected together by a third wire wrapped around the connection site 110. In a preferred embodiment, the third wire is a thin nitinol wire. One of the coils 106, 108 can be covered by a membrane material 112. In a preferred embodiment, the membrane material 112 comprises a mesh. The mesh material can be semipermeable, to allow blood flow and prevent the travel of clots. The mesh also can be impermeable to all materials.

In an alternate embodiment, one of the coils 106 can be covered with the semipermeable material and the other coil 108 can be covered by an impermeable material. In another preferred embodiment of the invention, the membrane material 112 is secured to the coil 108. The membrane 112 material can be secured to the coil 108 by an adhesive in one embodiment. The membrane 112 can also be melted onto or fused to the coil 108 in alternate embodiments. The membrane 112 can also contain a seam which wraps over the coil 108 and secures it to the coil 108. The membrane can also be sutured onto the stent strut. The stent strut can also be incorporated into the membrane. The mesh can be knitted or weaved around the stent strut.

In a preferred embodiment, the double coil stent 100 can have barbs or anchors 103 to prevent dislocation of the stent 100 after implantation. The barbs 103 can be welded to connection sites on the double coil stent 100. The barbs 103 can be made from an elastic material, to allow ease of placement inside a catheter. In a preferred embodiment, the barbs 103 are made from thin nitinol wires. In another preferred embodiment, the double coil stent 100 has a hook 105 to improve stability and prevent dislocation of the stent 100. The hook 105 can be attached to the second end 104 of the stent 100 and extend towards the first end 102.

The double coil stent 100 itself, in a preferred embodiment, is made of a wire material such as a nickel-alloy. The wire preferably comprises a shape memory material such that when the stent 100 is collapsed, it will return to a predetermined shape.

Figure 5:
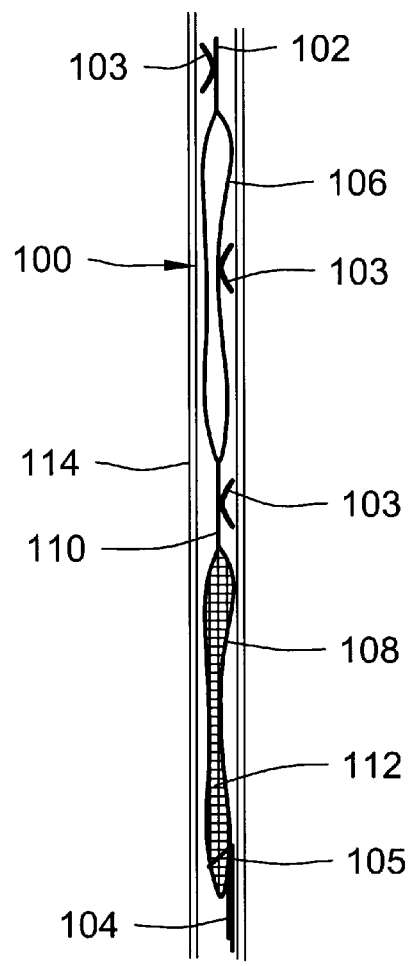
FIG. 5 illustrates a double coil stent in a non-expanded state.

FIG. 5 shows a double coil stent 100 in a non-expanded state within a catheter 114. The stent 100 can comprise a first coil 106 and a second coil 108 joined at a connection site 110. One of the coils can be covered by a membrane material 112, preferable a mesh material. In this embodiment, the first coil 106, the second coil 108, and the membrane material can be collapsed to fit the stent 100 within a catheter 114. The stent 100 can be compressed to fit into a catheter 114 having a diameter of 8 french (2.4 mm) for insertion into an aorta. However, the stent 100 can be compressed to fit into catheters from 0.5 mm to 5.0 mm in diameter generally, depending on the cross section of the artery to be treated and the diameter of the struts needed to create a firm suspension of the device. The connection site 110 between the first 106 and second 108 coils, in this embodiment, allows the coils 106, 108 to expand beyond their uncompressed 90-degree angulation. When the stent 100 is introduced into the catheter 114, the hook 105 can be positioned parallel to the second end 104 of the stent 100 and will not significantly increase the diameter of the collapsed stent 100.

Figure 6:
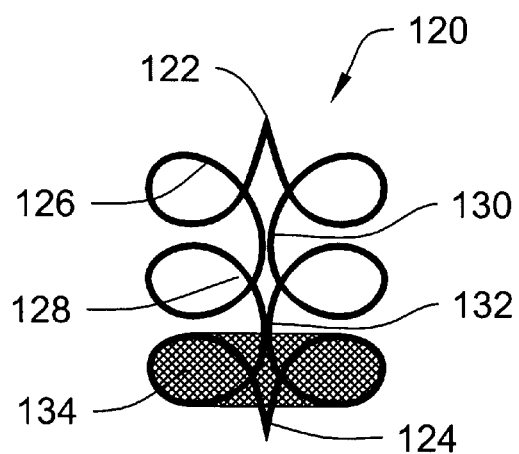
FIG. 6 shows a front view of an alternate embodiment of a double coil stent in an expanded state.
Figure 7:
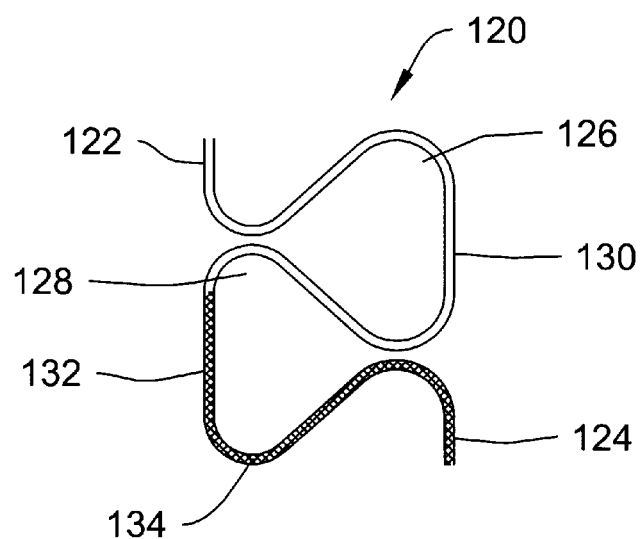
FIG. 7 shows a side view of an alternate embodiment of a double coil stent in an expanded state.

FIGS. 6 and 7 illustrate an alternate embodiment of a double coil stent 120. The double coil stent 120 comprises a shape memory material. In a preferred embodiment, this material can consist of metal wire. Other materials can be used, however, such as plastic. The stent 120 has a first end 122 and a second end 124. The stent material can form a first loop 126 and a second loop 128. The loops 126, 128 compensate for alterations of the material lumen or irregular vessel lumina. The loops 126, 128, in a preferred embodiment, are connected at a first connection site 130 and a second connection site 132, respectively. The stent 120 can also comprise a membrane material 134. In a preferred embodiment, the membrane material 134 is a mesh material. In this embodiment, the mesh can be semi-permeable to allow fluids, but not clots, to pass through a vessel. The mesh can also be impermeable to provide occlusion of a vessel. The mesh can also become impermeable over time, after being implanted as permeable, by the formation of blood clots at the mesh filaments to provide occlusion of a vessel.

Figure 8:
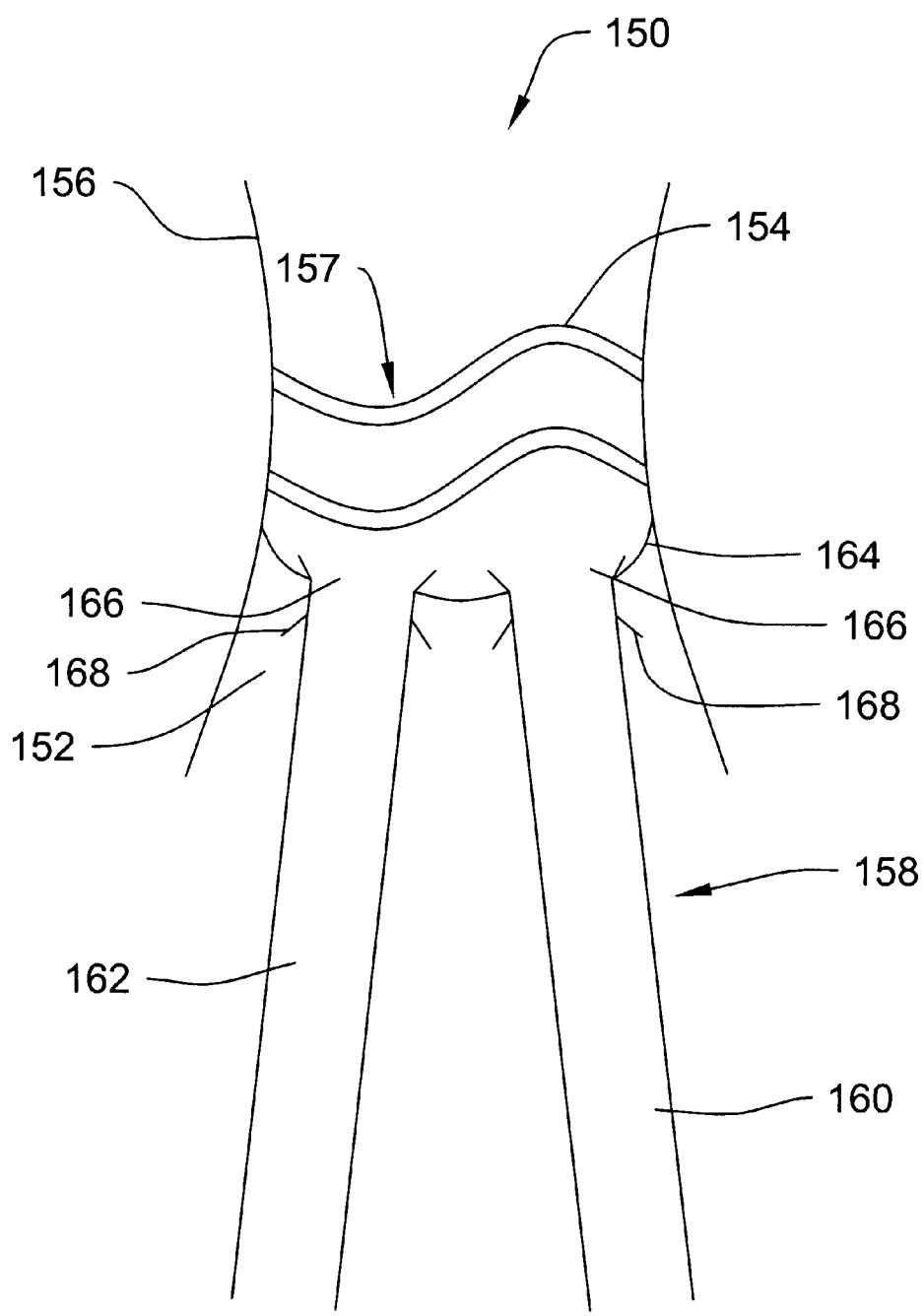
FIG. 8 illustrates an embodiment of a membrane attachment mechanism for a stent.
Figure 9:
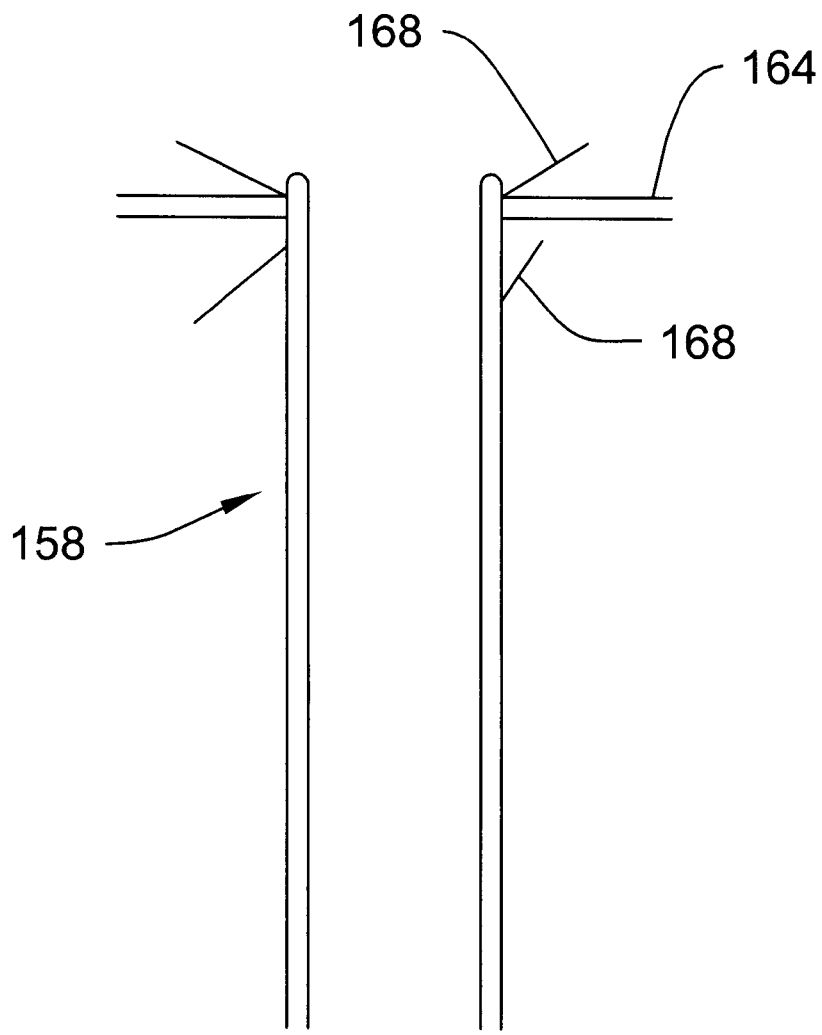
FIG. 9 illustrates an alternate embodiment of a membrane attachment mechanism for a stent.
Figure 10:
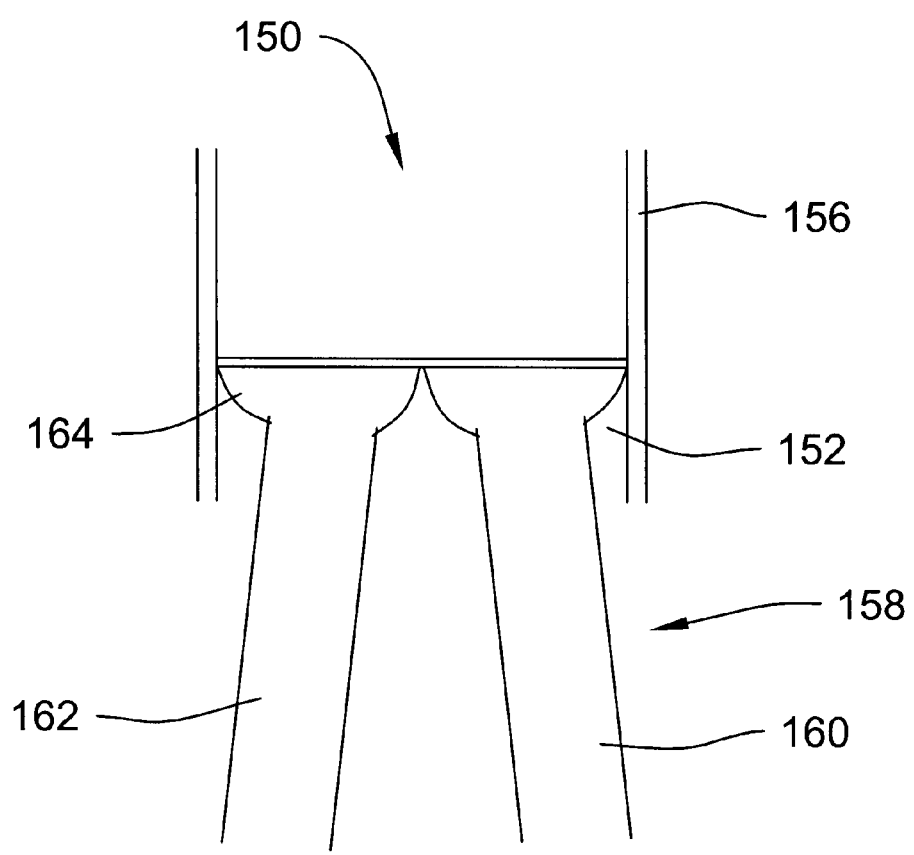
FIG. 10 illustrates an alternate embodiment of a membrane attachment mechanism for a stent.

FIGS. 8, 9 and 10 illustrate embodiments for a double coil stent with a bifurcation stent. FIG. 8 shows a double coil stent with a bifurcation stent 150 mounted within an aortic lumen 152. The stent 150 comprises a double coil stent 154 fitted to an aortic wall 156. In a preferred embodiment, the deployed double coil stent 154 comprises waves or undulations 157. The stent 150 can also comprise a bifurcation stent 158 having a first stent portion 160 and a second stent portion 162. In this embodiment, the membrane 164 of the double coil stent 154 comprises a dome shape which is accommodated to the flow dynamics of blood. The first 160 and second 162 stent portions of the bifurcation stent 150 are attached to the membrane 164 by funnel portions 166 on the ends of the stent portions 160, 162 to prevent any backsliding of the stent. The first 160 and second 162 stent portions can also comprise anchors 168, preferably barbs, below the membrane 164 to prevent sliding of the stent portions 160, 162 through the membrane 164. In its unexpanded state, the anchors 168 will lie parallel to the body of the bifurcation stent 158. When the double coil stent with the bifurcation stent 150 is removed from a catheter housing, the anchors 168 will move outwards because of their elastic tension and prevent sliding of the first or second stent portions 160, 162.

FIG. 9 shows an alternate embodiment of a double coil stent with a bifurcation stent. In this embodiment, the first 160 and second 162 stent portions of the bifurcation stent 158 comprise anchors 168 to prevent the stent 158 from sliding and becoming disengaged from the membrane 164.

FIG. 10 shows another alternate embodiment of a double coil stent with a bifurcation stent. In this embodiment, the membrane 164 comprises a double valley membrane. In this embodiment, the first 160 and second 162 stent portions of the bifurcation stent 158 can be secured to the membrane 164 by either a funnel portion or by anchors 168.

Figure 11:
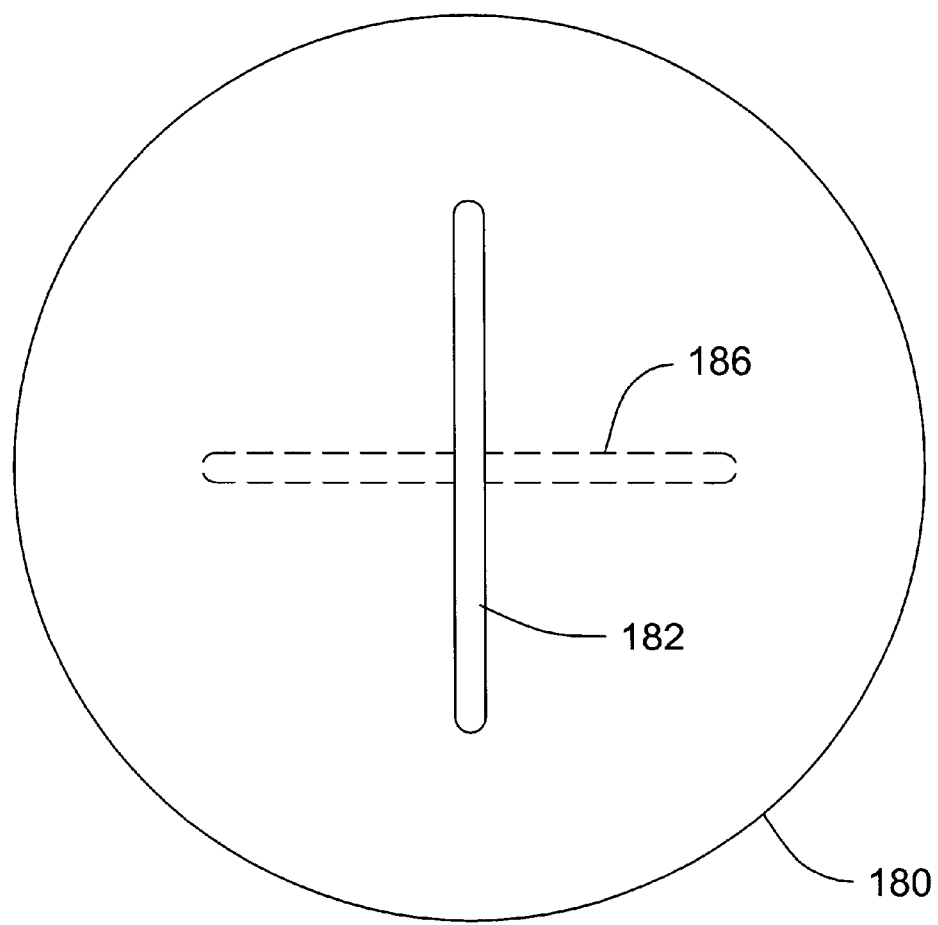
FIG. 11 shows an embodiment of a membrane that can have one or more slits.

FIG. 11 shows an embodiment of a membrane 180 to be used with a stent such as a double coil stent or with a bifurcation stent. In a preferred embodiment, the membrane 180 comprises a first slit 182 which dilates to receive an expanded stent. In an alternate embodiment, the membrane 180 can comprise two parallel slits to receive two stents. In an alternate embodiment, a second membrane fits above the first membrane 180 and comprises a second slit. The two membranes form a tight seal between the occluder lumen walls. In a preferred embodiment, the membranes are silicone.

Figure 12:
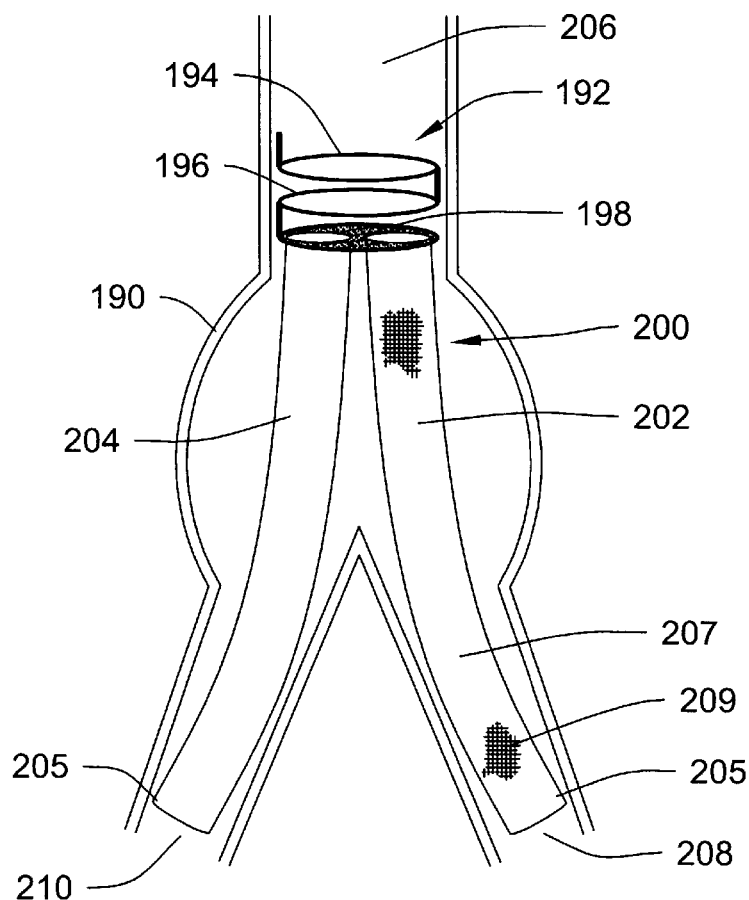
FIG. 12 shows a double coil stent with a bifurcation stent engaged at an aneurysm site.

FIG. 12 shows a double coil stent with a bifurcation stent engaged at an aneurysm site 190. The double coil stent 192 in this embodiment comprises a first coil 194, a second coil 196, and a membrane 198. The double coil stent 192 secures the bifurcation stent 200 within the aorta. The bifurcation stent 200 comprises a first stent portion 202 and a second stent portion 204 which are mounted within the membrane 198. The first 202 and second stent 204 portions of the bifurcation stent carry blood from the aorta 206, past the aneurysm site 190 and to the first 208 and second 210 bifurcation portions. This process reduces the pressure at the aneurysm site 190, helps prolong the life of the aneurysm and reduces the risk of rupture of the aneurysm.

In a preferred embodiment, the first stent portion 202 and the second stent portion 204 are arced to provide for ease of insertion into the first 208 and second 210 bifurcation portions, respectfully. When inserted into the bifurcation portions 208, 210, the stent portions 202, 204 form a fluid seal 205. The seal substantially reduces or eliminates endoleakage or discharge of the fluid flowing through the stent portions 202, 204. In another preferred embodiment, the first 202 and second 204 stent portions are comprised of a mesh material 209. This material can comprise a fabric material. The material can also comprise a plastic material. In another preferred embodiment, the mesh material 209 is covered by a second material 207. The second material 207 provides for strength of the stents 202, 204 while allowing them to retain flexibility.

Figure 13:
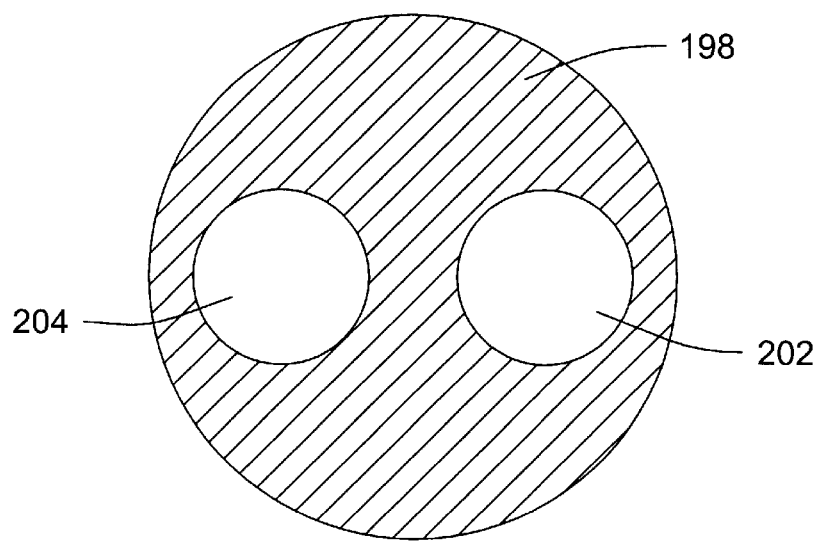
FIG. 13 shows a top view of the prosthesis illustrated in FIG. 12.

FIG. 13 illustrates a top view of the membrane 198 having the first 202 and second 204 bifurcation stent portions secured therein. In this embodiment, the membrane occludes blood flow through the aneurysm 190 and forces the blood to flow through the first 200 and second 204 bifurcation portions.

Figure 14:
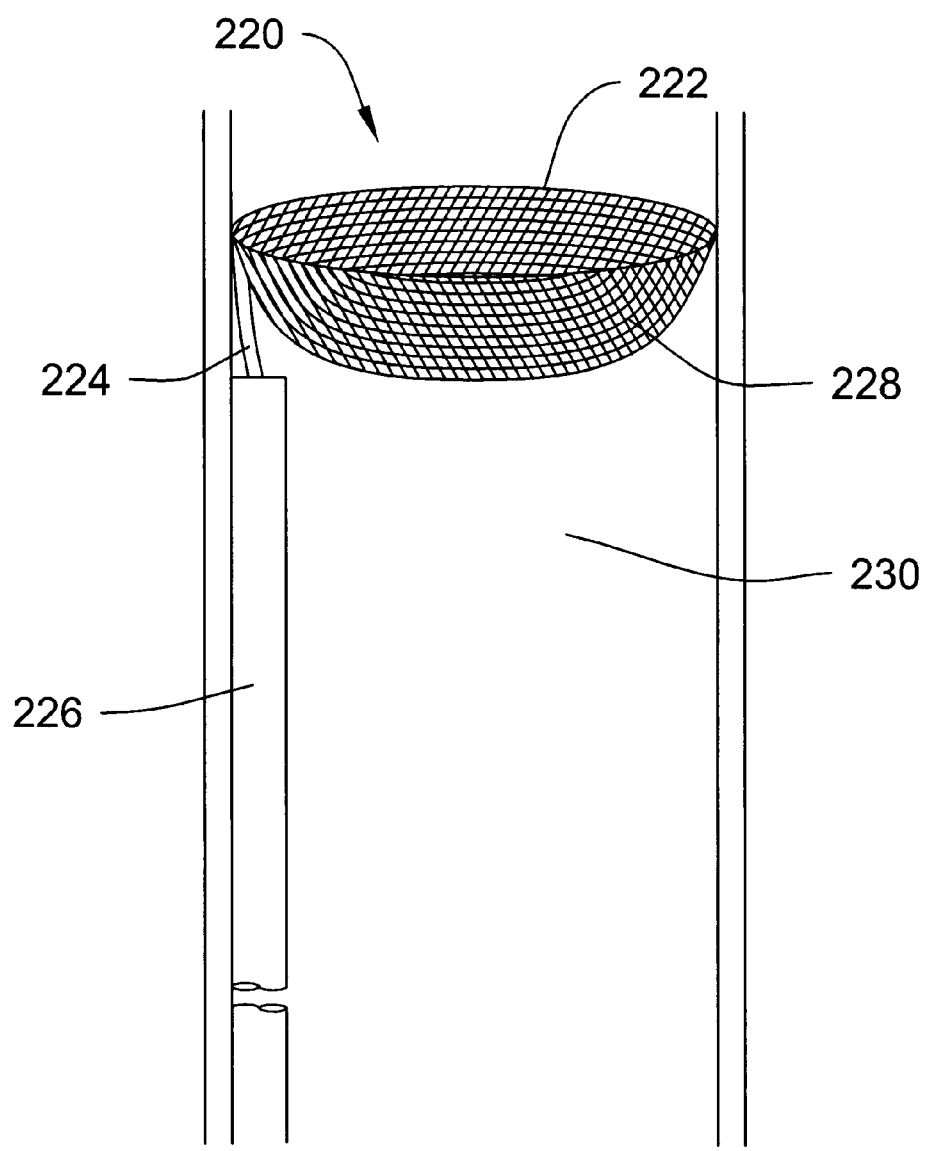
FIG. 14 illustrates an embodiment of a temporary membrane filter.

FIG. 14 illustrates a removable membrane mesh filter 220. The filter 220 comprises a coil loop 222 attached to a coupler 224 which can be deployed and withdrawn through a catheter 226. The coupler 224 can be either flexible or rigid. The coupler 224 can also provide for axially distancing stabilizing member from frame. The coil loop 222 comprises a membrane 228. In a preferred embodiment, the coil loop 222 is a nickel-alloy wire loop. In another preferred embodiment, the membrane 228 is a textile mesh.

The filter 220 can comprise a basket shape for the membrane 228 to allow for clot removal. The filter 220 can also be inserted from below to remove debris. In an alternate embodiment, lysing agents can be delivered through the catheter in order to perform clot lysis. The removable membrane mesh filter 220 can be deployed in an aorta lumen 230 to serve as a filter in the case of an emergency treatment such as an embolism. An impermeable membrane can be used to occlude the aorta to provide emergency treatment of a ruptured aneurysm.

Figure 15A:
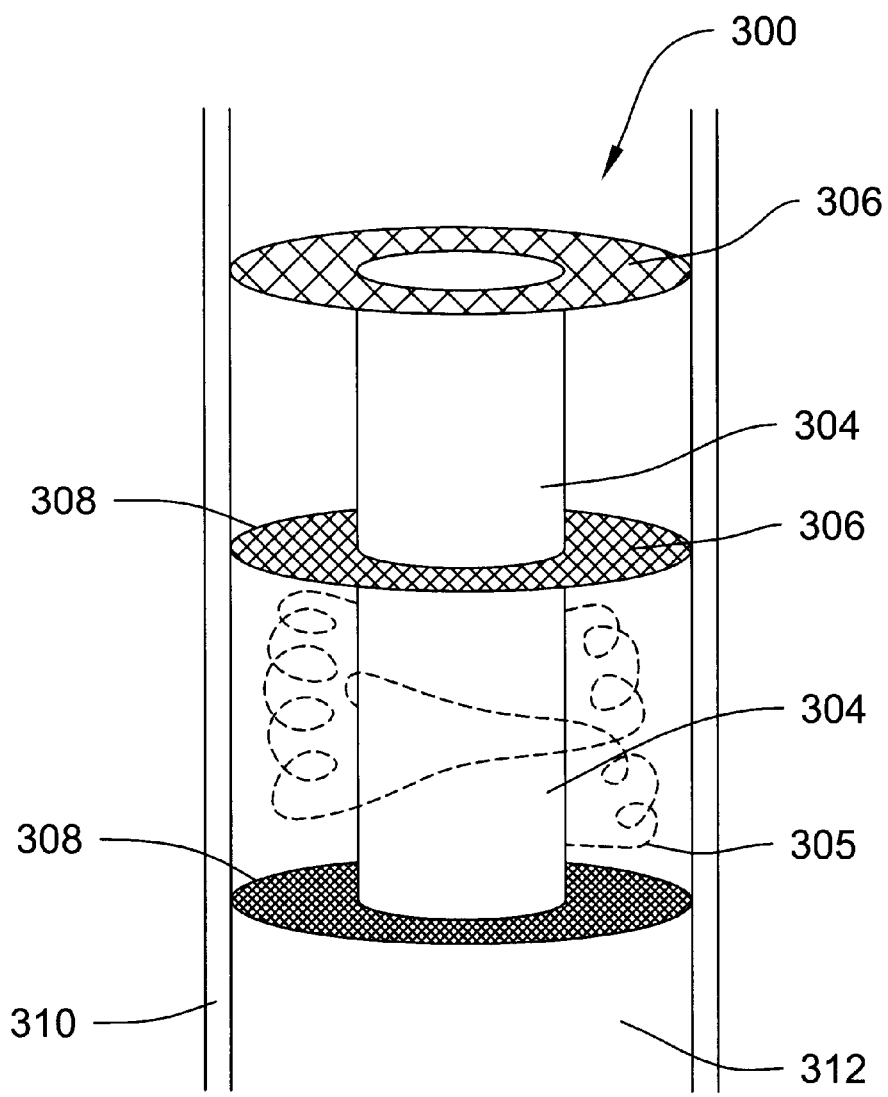
FIG. 15A illustrates coaxial stents attached to multiple filters.

FIG. 15A illustrates an alternate embodiment of the invention comprising a coaxial stent prosthesis 300. The coaxial stent 300 comprises a plurality of stents 304 coaxially mounted to a plurality of membranes 306. In a preferred embodiment, two stents 304 are mounted coaxially to three membranes. The membranes can be affixed to a wire material 308. When deployed, the wire material 308 of the prosthesis 300 becomes secured to the wall 310 of a lumen 312. In a preferred embodiment, the membranes 306 comprise a filter mesh. In an alternate embodiment, the membranes 306 comprise a non-permeable material. The membranes 306 can have different diameters, corresponding to the diameters of an aneurysm. Thus, the membrane 306 in the middle of FIG. 15A can have a larger diameter than the upper and lower membrane. When deployed, this embodiment can divide an aneurysm into two chambers. Blood can thus reenter into just one chamber of the aneurysm instead of the entire aneurysm. Reperfusion of the aneurysm by lumbar arteries or by the inferior mesenteric arteries can be of less importance. The chambers created between the membranes 306 can be filled with an adhesive such as a curable polymer to provide for a firm connection of the membranes to the aortic wall.

Figure 15B:
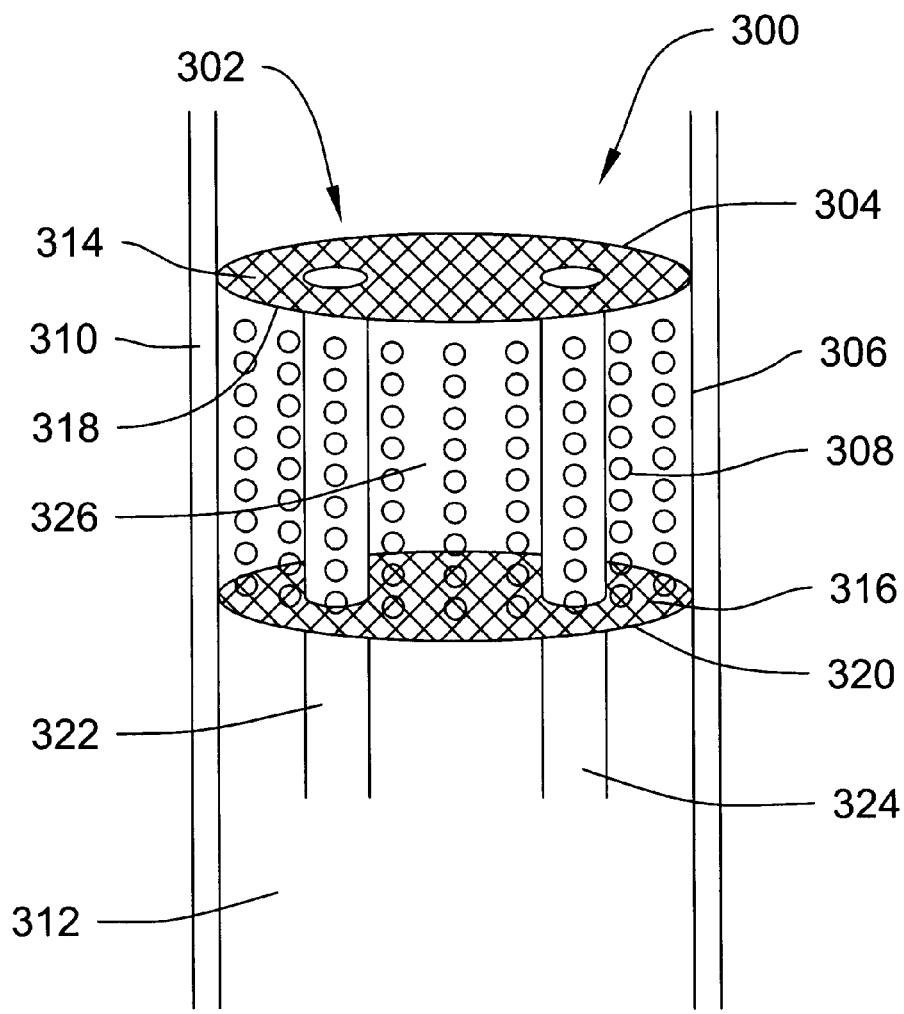
FIG. 15B shows an alternate embodiment for a mesh with attached stent.

FIG. 15B shows another alternate embodiment of a double coil stent with a bifurcation stent 300. In this embodiment, the double coil stent with a bifurcation stent 300 is mounted within an aortic lumen 312. The stent 300 has a double coil stent 304 fitted to an aortic wall 310. The double coil stent 304 has a first wire loop 318 and a second wire loop 320 covered by a first membrane 314 and a second membrane 316, respectively. The double coil stent 304 also has a wire strut 306 connecting the first 318 and second 320 wire loops. In this embodiment, a bifurcation stent 302 having a first bifurcation portion 322 and a second bifurcation portion 324, is attached to the double coil stent 304, through the first 314 and second 316 membranes. The bifurcation stent 302 passes through both membranes 314, 316 to form an improved connection for and prevent any dislocation of the first 322 or second 324 bifurcation portions.

The space 326 between the first wire loop 318 and the second wire loop 320 can be filled with a polymer 308. The polymer can cure in this space 326 which provides a firm connection among the aortic wall 310, the bifurcation stent 302 and the membrane or double coil stent 304. The polymer 308 can be installed by perforation of the second membrane 316 with a distally introduced catheter. Through the end hole of the catheter, the polymer 308, in its fluid state, can thereby be injected into the space 326. The polymer 308 can be, but is not limited to, either polymer silicone, acrylate glue, ETHIBLOC™, gelatine or gelatine sponge. In a preferred embodiment, the polymer 308 does not act as a plug, but functions to connect any implanted parts to a vessel wall. The polymer can assist in sealing against leakage.

In addition to a polymer curing in the chamber between the membranes, also, note the use of wire coiling 305 instead of, or in addition to the polymer. Wire coiling is a procedure to treat aneurysms. A surgeon can introduce wire coils into the aneurysmal sack to create thrombosis within the peripheral parts of the aneurysm and to provide flow within the centre. In case of wire coils within one of the chambers as shown in FIG. 15B, the blood flow is provided through the stent in the centre of the chamber without any disturbances by the coils surrounding the stents. Wire coils have the advantage of easy handling. The coils can be inserted through a catheter like the polymer. Migration of the coils is unlikely, particularly when used with a polymer. The polymer can embolize before curing. Embolization coils including a wire with a rough surface e.g. wool filaments creates a thrombosis within the chamber.

Figure 16:
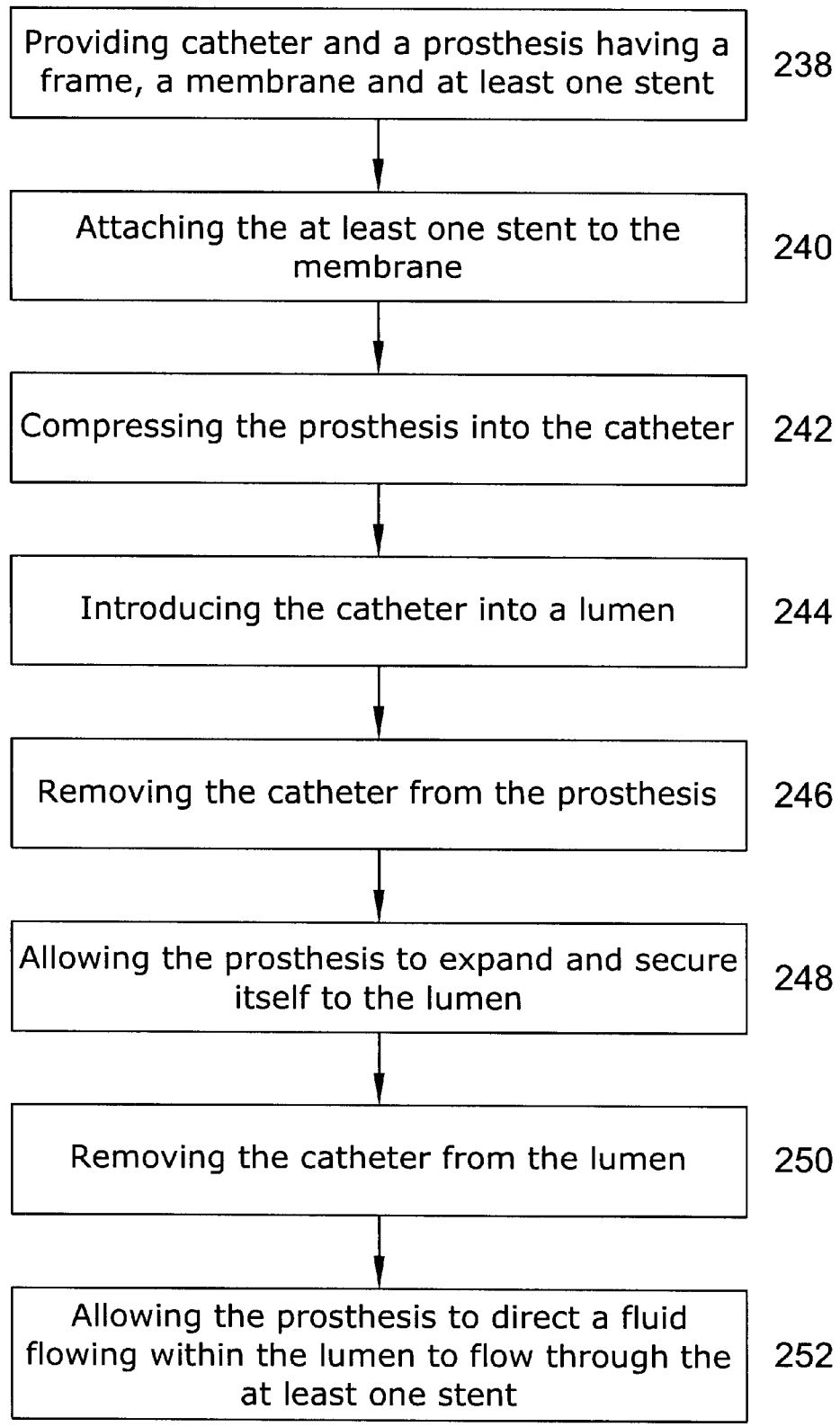
FIG. 16 shows a schematic representation of a method for treating a body lumen.

FIG. 16 shows a schematic representation of a method for treating a body lumen. First, the user provides a catheter and a prosthesis having a frame, a membrane and at least one stent 238. Next, the user attaches the at least one stent to the membrane 240. Next, the user compresses the prosthesis into the catheter 242 and introduces the catheter into a lumen 244. The user can then remove the catheter from the prosthesis 246 and allow the prosthesis to expand and secure itself to the lumen 248. Next, the catheter can be removed from the lumen 250. Lastly, the prosthesis is allowed to direct a fluid flowing within a lumen to flow through at least one stent 252. In a preferred embodiment, the at least one stent directs the fluid across an aneurysm.

Figure 17:
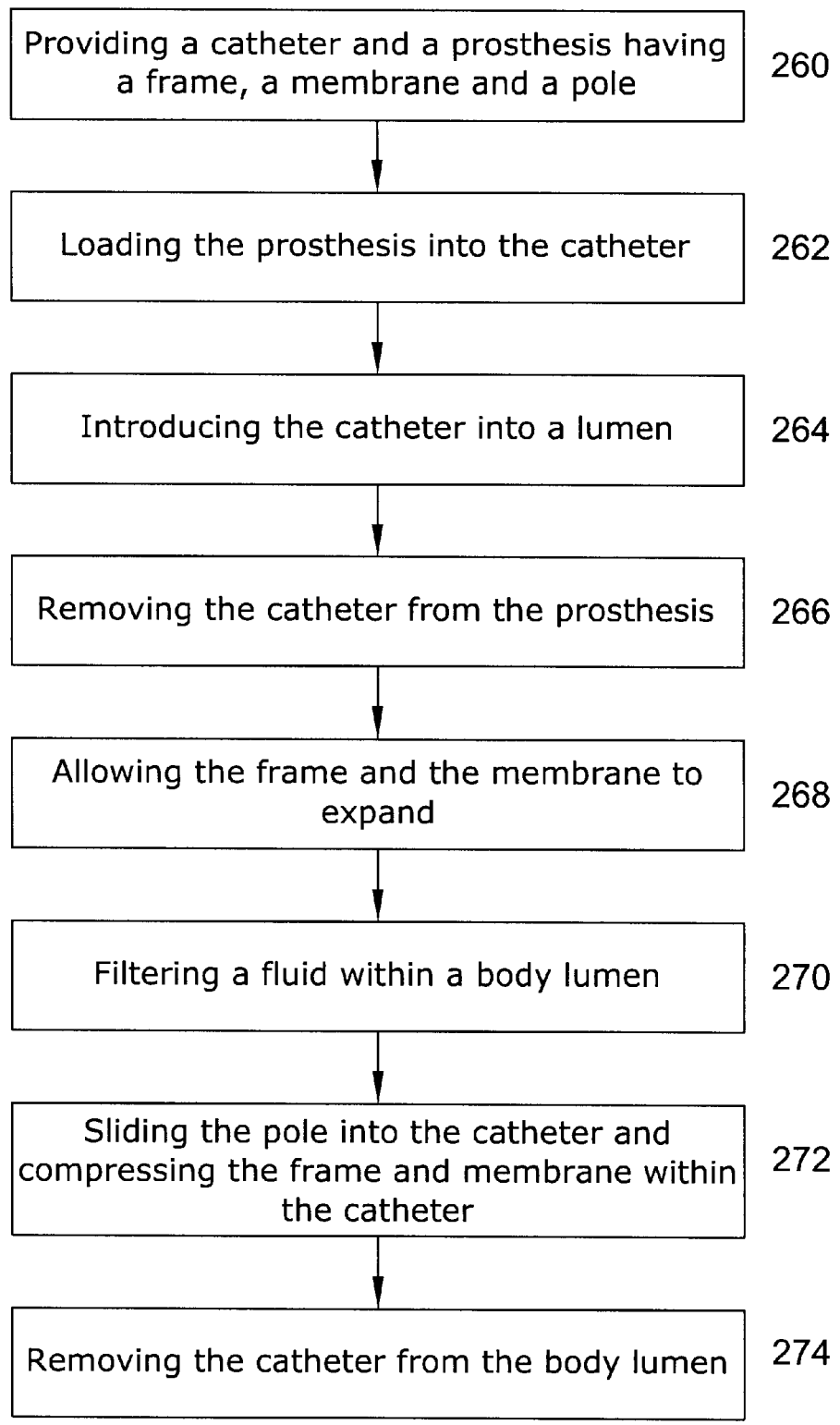
FIG. 17 illustrates a schematic representation for deploying a temporary prosthesis within a body lumen.

FIG. 17 illustrates a schematic representation for deploying a temporary prosthesis within a body lumen. First, the user provides a catheter and a prosthesis having a frame, a membrane and a connector 260. Next, the user loads the prosthesis into the catheter 262 and introduces the catheter into a lumen 264. The user can then remove the catheter from the prosthesis 266 and allow the frame and membrane to expand 268. Next, a fluid flowing through the lumen can be filtered by the prosthesis 270. When the filtering process has been completed, the user can slide the connector into the catheter and compress the frame and membrane within the catheter 272. The user can then remove the catheter from the lumen 274. In a preferred embodiment, the membrane comprises a mesh material.

Figure 18:
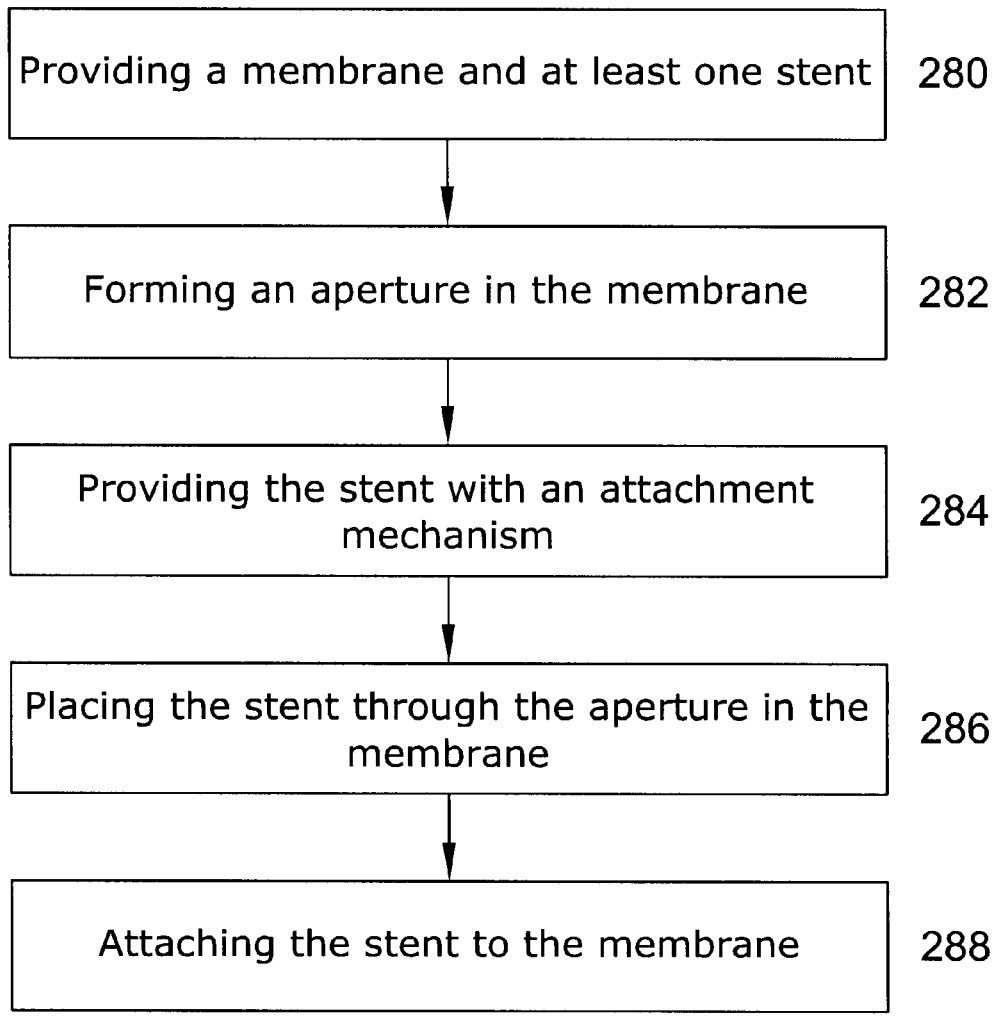
FIG. 18 illustrates a method for attaching at least one stent to a membrane.

FIG. 18 illustrates a method for attaching at least one stent to a membrane. First, the user provides a membrane and at least one stent 280. Next, an aperture is formed in the membrane 282 and the stent is provided with an attachment mechanism 284. The stent can then be placed through the aperture in the membrane 286 and attached to the membrane 288. In one preferred embodiment, the attachment mechanism comprises an anchor. In another preferred embodiment, the attachment mechanism comprises a funnel portion connected to the stent.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A prosthetic device comprising:
   a frame comprising a plurality of struts extending radially outward and a membrane extending over the plurality of struts, the frame having a perimeter;
   at least one stent having a lumen therethrough, the at least one stent having a proximal end and a distal end, the proximal end of the at least one stent connected to an opening in the membrane;
   a securing element located proximally of the frame, the securing element having at least one point of attachment to the frame at a location spaced away from the perimeter of the frame.

2. The prosthetic device of claim 1 wherein the frame and the membrane have a delivery position and an expanded position.

3. The prosthetic device of claim 2 wherein the delivery position has a diameter of 12 French or less.

4. The prosthetic device of claim 1 wherein the frame further comprises a shape memory material.

5. The prosthetic device of claim 1 wherein the plurality of struts further comprise a plurality of loop shapes.

6. The prosthetic device of claim 1 wherein the membrane further comprises a mesh.

7. The prosthetic device of claim 1 wherein the membrane further comprises a non-permeable material.

8. The prosthetic device of claim 1 wherein the membrane extends beyond the perimeter formed by the plurality of struts.

9. The prosthetic device of claim 1 wherein the at least one stent further comprises a flexible shape memory material.

10. The prosthetic device of claim 1 wherein the stent further comprises a mesh material.

11. The prosthetic device of claim 1 wherein the proximal end of the stent further comprises a taper.

12. The prosthetic device of claim 11 wherein the taper of the stent decreases to a diameter at the proximal end by a range of 5%–15%.

13. The prosthetic device of claim 1 wherein the securing element further comprises a plurality of anchors.

14. The prosthetic device of claim 1 wherein the securing element further comprises a shape memory material.

* * * * *